United States Patent [19]

Kunimi et al.

[11] Patent Number: 5,068,467
[45] Date of Patent: Nov. 26, 1991

[54] PROCESS FOR PRODUCTION OF SOLID SORBITOL

[75] Inventors: Yuji Kunimi; Akihiko Tabata, both of Ushiku; Yatsuka Fujita, Nishinomiya, all of Japan

[73] Assignee: K.K. Ueno Seiyaku Oyo Kenkyujo, Osaka, Japan

[21] Appl. No.: 552,361

[22] Filed: Jul. 12, 1990

Related U.S. Application Data

[63] Continuation of Ser. No. 312,998, Feb. 21, 1989, abandoned.

[30] Foreign Application Priority Data

Feb. 20, 1988 [JP] Japan ................................. 63-38349

[51] Int. Cl.$^5$ ....................... C07C 29/78; C07C 31/26
[52] U.S. Cl. ..................................... 568/852; 568/868
[58] Field of Search .............................. 568/868, 852

[56] References Cited

U.S. PATENT DOCUMENTS

| | | | |
|---|---|---|---|
| 3,330,874 | 7/1967 | Shannon | 260/637 |
| 3,342,856 | 9/1967 | Marquis | 562/37 |
| 4,252,794 | 2/1981 | DuRoss | 568/852 |

FOREIGN PATENT DOCUMENTS

| | | |
|---|---|---|
| 34562 | 11/1988 | Austria . |
| 32288 | 7/1981 | European Pat. Off. . |
| 2059246 | 7/1971 | Fed. Rep. of Germany . |
| 1287509 | 8/1972 | United Kingdom . |
| 1481846 | 8/1977 | United Kingdom . |
| 2046743 | 11/1980 | United Kingdom . |

*Primary Examiner*—J. E. Evans
*Attorney, Agent, or Firm*—Sughrue, Mion, Zinn, Macpeak & Seas

[57] ABSTRACT

The present invention provides an improved method of producing solid sorbitol which hardly cakes even in long storage, in which seed crystals are dispersed in melted sorbitol at a temperature that the melted sorbitol does not solidify but the seed crystals do not melt, and cooled to about 50° to 85° C., kept at said temperature for a given period and then cooled again.

10 Claims, No Drawings

PROCESS FOR PRODUCTION OF SOLID SORBITOL

This is a continuation of application Ser. No. 07/312,998 filed Feb. 21, 1989, now abandoned.

BACKGROUND OF THE INVENTION

The present invention relates to a process for production of solid sorbitol.

In general, sorbitol can be produced by the hydrogenation of glucose which can be obtained by the hydrolysis of starch. As the sorbitol obtained by such a process contains much amount of water, it is concentrated to about 70% by weight of solid or further dried to powder for commercial use. The concentrated sorbitol is broadly used for general industrial use because its price is extremely cheaper than that of the powdered sorbitol. The concentrated sorbitol, however, cannot be used in some areas such as pharmaceuticals, cosmetics, or food restricted in the use of water, or in such a cold place that the concentrated sorbitol becomes too viscous to be weighed or is frozen or crystallized. In such areas powdered sorbitol may be conveniently used because it does not contain water or easy to weigh (possible use of a general automatic weigher). Sorbitol powder obtained by simply drying a concentrated sorbitol solution and powdering it has a tendency to form a mass or a cake with time even if it is stored under dry condition, becomes difficult to be dealt, and loses the commercial validity in its appearance.

Accordingly, methods of production of sorbitol powder which hardly forms cakes, or methods of preventing the sorbitol powder from caking have been proposed.

In one of the simplest methods of production of non-caking sorbitol powder, crystalline sorbitol (seed) is added to melted dried sorbitol, and then gradually cooled to 30° C. or lower over long time, for instance, over about 24 hours to give powder. This process needs too long time to be applied to an industrial use.

As a method to improve the above process there is proposed in Japanese Patent Publication No. 36206/1974 that a concentrated aqueous solution of sorbitol is continuously supplied with seeds into a specific mixer, mixed, discharged, and then held at room temperature. In this method a long cooling time is also necessary to obtain a sorbitol powder having no tendency of caking.

As another method of preventing the sorbitol powder from caking it is proposed in Japanese Patent Application KOKAI No. 133229/1981 that a sorbitol powder is mixed at a temperature of 50° C. or more but lower than the melting point. The principle of this method is to change the surface condition of sorbitol powder. A problem of this method is that the sorbitol once powdered is necessarily treated again.

SUMMARY OF THE INVENTION

The object of the present invention is to provide a method of production of stable crystalline sorbitol powder or granule having substantially no tendency to form a cake with time. The process is simple and can be made in a short time. In said method seed crystals are dispersed with stirring into melted sorbitol kept at a temperature that the sorbitol does not solidify and the seeds do not melt, cooled to about 50° C. to about 85° C., and then kept at said temperature for a given period.

DETAILED DESCRIPTION OF THE INVENTION

The present invention relates to a method of production of solid sorbitol which comprises dispersing seed crystals into melted sorbitol with stirring at a temperature that the sorbitol does not solidify and the seed crystals do not melt, cooling the dispersion to about 50° C. to about 85° C., keeping it at said temperature for a given period, and then cooling it to a room temperature.

The melted sorbitol usable in the present invention may be a melted one which is obtained by drying an aqueous concentrated solution of sorbitol and keeping the temperature that the sorbitol does not solidify, or a melted one which is obtained by melting again a dried and solidified sorbitol such as non-crystalline pellet, block or plate; further it may include a melted one obtained by re-melting sorbitol powder of unstable crystalline condition. The melted sorbitol usable in the present invention may contain water of less than 10 per cent by weight, and more preferably 1% by weight or less.

The seed crystals may be added into the melted sorbitol with stirring. If the temperature of the melted sorbitol is higher than the melting point of the seeds, they are melted, and the object of the present invention cannot be achieved. Therefore, the temperature of the melted sorbitol should be controlled at a temperature slightly lower than the melting point of the seed crystals. Usually, as the seed crystals crystallized sorbitol (m.p. about 96° C.) are preferably used, and in such case the temperature of the melted sorbitol at addition of the seeds may be preferably controlled at, for instance, about 70°-95° C., and at this temperature the seeds do not melt and the melted sorbitol can be agitated without complete solidification. Such a temperature may be controlled naturally or compulsorily cooled, but preferably controlled by the addition of seeds such as crystalline sorbitol powder.

Though preferable seed crystals are crystallized sorbitol powders, which may be used with fats, oils and/or surface active agents as mentioned hereinafter. In the present invention the seed crystals are not restricted to pure sorbitol, and may include other ingredients, for example, powders of reduced saccharides such as mannitol, maltitol, xylitol and the like.

The amount of the seed crystals to be added may be about 1 to 50 per cent by weight, preferably about 5 to 50 per cent by weight, more preferably about 5 to 30 per cent by weight based on the melted sorbitol. When the amount of the seeds is less than 5 per cent by weight, comparatively long period is sometimes needed to crystallize the sorbitol.

In order to prepare the solid sorbitol powders of the present invention into the melted sorbitol the seed crystals are added with stirring and dispersed as the temperature of the melted sorbitol is controlled at 70° to 95° C. Under this condition crystals of sorbitol are deposited on the surface of the seed crystals. When this mixture is naturally or compulsorily cooled to a temperature of from about 50° to 85° C. (first cooling process), and held at a temperature of about 50° to 85° C., preferably about 60° to about 85° C., more preferably about 65° to about 80° C. for about 5 minutes or more, preferably about 10 minutes or more (aging process), the formation of crystal progresses. There is a fairly intimate relationship between the temperature and period at the aging process, for instance, in case that 20 per cent by weight of the seed crystals are used, crystallized sorbitol having especially suitable properties can be obtained when it is treated at 80° C. for 4 hours, at 75° C. for 2 hours, at 65°-70° C. for one hour or at 60° C. for 7 hours.

Such a treatment (aging process) may be achieved by holding a half-solidified sorbitol in which the seed crystals are dispersed at a given temperature for a given period in a suitable shape such as pellet, flake, plate and the like.

The sorbitol subjected with such a treatment may be rapidly or gradually cooled to room temperature or rapid and gradual cool may be alternately repeated. Such a cooling process (secondary cooling process) may be carried out by any methods. But in the aspect of the production efficiency or productivity rapid cooling is recommendable. Preferable cooling rate is 50°-200° C./hr.

Crystalline sorbitol having a suitable shape such as pellet, flake, plate and the like obtained according to such a process may be powdered or granulated if necessary. The powdered or granulated sorbitol thus obtained hardly cakes even in long storage. Accordingly, solid sorbitol in the present invention includes not only a powdered or granulated sorbitol but also a suitably shaped sorbitol such as pellet, flake, plate and the like before powdering or granulating.

If the melted sorbitol is directly cooled after the seed crystals are added without the treatment (aging process), it is incompletely crystallized, as the result of which the cooled sorbitol naturally and gradually rises in temperature again when held at room temperature or after powdered or granulated, and then the obtained solid sorbitol cakes with time.

In the production of solid sorbitol as aforementioned the temperature of the melted sorbitol is partially reduced by the addition of seed crystals, and partial hardening of the sorbitol is liable to progress, so that the seed crystals unhomogeneously may disperse in the melted sorbitol. Further, as the viscous of the melted sorbitol rapidly increases according to the decrease of temperature, the viscosity control of melted sorbitol becomes difficult when the seed crystals are added and dispersed in the melted sorbitol. Therefore, meticulous care should be rayed in the stirring condition, addition rate of seed crystals, amount of the seed crystals and the like.

In order to solve the above problems fats, oils and/or surface active agents (these materials are simply referred to as addition agents hereinafter, may be preferably added to the melted sorbitol. By the addition of the addition agents an emulsion of sorbitol and the addition agents are formed, and the fluidity of the melted sorbitol can be maintained up to a comparatively lower temperature. Therefore, the melted sorbitol can be easily stirred even if the temperature is lowered by the addition of the seed crystals, so that a partial solidification can be avoided, and uniform dispersion of the seed crystals can be easily achieved. Accordingly, better results can be obtained by the use of the addition agents even in the use of a small quantity of seed crystals in comparison with the alone use of melted sorbitol. Further, a large quantity of seed crystals can be used, if the addition agents are used.

Examples of the fats or oils of the present invention may include vegetable oils, animal oils, hardened oils, mineral oils, waxes (esters of higher fatty acids and higher fatty alcohols) and the like. Preferable one is a vegetable oil such as rapeseed oil, soybean oil, cottonseed oil, palm oil, corn oil, rice bran oil, safflower oil, peanut oil, olive oil, castor oil, jojobabean oil and the like.

The surface active agents of the present invention are not restricted, but ones which are accepted as additives for foods, pharmaceuticals or cosmetics are preferable, because the solid sorbitol is often used for such areas.

Examples of the surface active agents may include glycerol fatty acid esters such as monoglycerides, diglycerides; sugar fatty acid esters; sorbitan fatty acid esters; propyleneglycol fatty acid esters; pentaerythritol fatty acid esters; polyglycerol fatty acid esters; polyoxyethylene sorbitan fatty acid esters; polyoxyethylene alkyl ethers; lecithin, soap of higher fatty acid; saponin; casein and the like. Almost all the surface active agents can be used if the solid sorbitol of the present invention is used in areas other than the foods, pharmaceuticals or cosmetics. Examples of these surface active agents are polyoxyalkylene alkyl ethers, polyoxyalkylene alkylaryl ethers, polyoxyalkylene alkylamides, polyoxyethylene/polyoxypropylene random or block copolymer, or sulfates of the polyoxyalkylene ether type nonionic surface active agents, fatty acid esters of polyoxyalkyleneglycols, alkylalkanolamides (reaction products of fatty acids and diethanolamine) and the like.

The above addition agents may be introduced into the melted sorbitol by previously added to concentrated sorbitol which is followed by drying, or by added to the melted sorbitol before the addition of seed crystals. The addition agents containing seed crystals dispersed may be mixed into the melted sorbitol.

The amount of addition agents to be used is preferably 0.5% by weight or more, especially 1% or more based on the melted sorbitol though depended on the varieties of the addition agents. The use in more than 30% by weight is meaningless. In the aspect of the purity of solid sorbitol the addition agents may be preferably used as little as possible so far as the effect of the addition agents can be expressed. In, however, the production of the solid sorbitol intended to additives for surimi (minced fish meat) the solid sorbitol may be contains much more addition agents, because the additives usually contain a much quantity of addition agents.

The present invention will be illustrated according to the following Examples.

EXAMPLE 1

Into a small kneader (2 liters) equipped with a jacket concentrated sorbitol (water content 1% or less) 400 g was charged and kept at 92° C., into which sorbitol powder 40 to 120 g (10-30% by weight based on the concentrated sorbitol) was added as a seed crystal, and then continuously blended. When the seed crystals were homogeneously dispersed, the mixture was taken out of the kneader, and then pressed over in thickness of from about 3 to about 5 mm on a lagged stainless steel plate. The obtained solid sorbitol flake was maintained in a thermostatic chamber controlled at 50° C.-80° C., and the sorbitol samples which were sampled every given times were thermoanalyzed by Thermal Analysis System SSC-5000 (produced by Seiko Instruments Inc.), and the time necessary for the sorbitol to form a stable crystal was determined. When the exotherm or endotherm excepting the endothermic peak due to the melt becomes 0, it was evaluated as the stable crystals being formed.

Thermal Analysis System

SSC 5000

Differential Scanning Calorimeter
Type: DSC 200
Cell: P/N50-020 AL φ5 PAN
Range of scanning: 10°-130° C.
temperature increasing rate: 4° C./min The results were shown in Table 1. As apparent from Table 1, when the seed crystals were added 10% by weight or more, especially 20% by weight or more, the remarkable effect of the thermal treatment for the formation of stable crystals is observed.

TABLE 1

| quantity of seed* | temperature for treatment | | | | state of mixture before treatment |
|---|---|---|---|---|---|
| | 50° | 60° C. | 70° C. | 80° C. | |
| | period for formation of stable crystal | | | | |
| 10 wt. % | 48 h | 48 h | 4 h | 8 h | soft rice cake like |
| 20 wt. % | 24 h | 7 h | 1 h | 4 h | hard rice cake like |
| 30 wt. % | 10 h | 3 h | 20 m | 2 h | fairly hard rice cake like |

*The quantities of the seed to be added are expressed by the percentage to the concentrated sorbitol.
h: hour
m: minute

EXAMPLE 2

The solid sorbitol was subjected with the treatment (aging process) under the condition that the quantity of seed was 20wt. %, temperature for treatment was 70° C., and period of the treatment was one hour according to the same manner as in Example 1, granulated, and then kept in a sealed glass vessel at 37° C. Even after 3 months the solid sorbitol granules did not cake.

On the other hand a solid sorbitol obtained according to the same manner as in the above except omitting such a treatment (aging process) was difficultly granulated, and cake was observed after only 3 days when the granule was kept in the same manner as the above.

EXAMPLE 3

Sorbitol powder 400 g was melted at 110° C., to which glycerol fatty acid ester (origin: cottonseed oil) 4.0 g were added with stirring. The mixture was agitated by a homogenizer for 10 minutes to disperse to particles of 10 micrometer. The dispersion obtained was charged into a small kneader (2 liter) with a jacket, and kept at 90° C. with kneading, to which sorbitol powder 80 g (20% by weight to the melted sorbitol) was added as seed crystals, and blended for 3 minutes. The resultant was pressed over on stainless steel plates kept at given temperatures of from 5° to 85° C. respectively at the thickness of 3 to 5 mm and solidified. The plate like sorbitol obtained was kept in thermostatic chambers controlled at given temperatures of from 5° to 85° C., sampled every given times, and analyzed by Thermal Analysis System SSC 5000 to determine the time necessary for the sorbitol to form a stable crystal.

The same processes were repeated using rapeseed oil (21.1 g), and sorbitan monooleate (44.4 g) respectively as an oily substance instead of the glycerol fatty acid ester, and without any addition agents. The results were shown in Table 2.

TABLE 2

| | temperature for treatment and time for formation of stable crystals | | | | | | | | | state of sorbitol before treatment |
|---|---|---|---|---|---|---|---|---|---|---|
| | 5° C. | 40° C. | 50° C. | 60° C. | 65° C. | 70° C. | 75° C. | 80° C. | 85° C. | |
| (1) | >48h | 24h | 4h | 1h | 30m | 15m | 15m | 1h | 4h | very soft rice cake like |
| (2) | >48h | 48h | 8h | 2h | 1h | 30m | 30m | 2h | 6h | soft rice cake like |
| (3) | >48h | 36h | 8h | 1h | 30m | 15m | 30m | 1h | 4h | soft rice cake like |
| (4) | >48h | >48h | 24h | 7h | 1h | 1h | 2h | 4h | 10h | hard rice cake like | oily substance used in:
(1): glycerol fatty acid ester (origin: cottonseed oil),
(2): rapeseed oil,
(3): sorbitan monooleate,
(4): none
h: hour
m: minute As apparent from Table 2 the addition of the addition agents can remarkable shorten the time necessary for the formation of stable crystals, especially at the treatment of from 60° C. to 80° C. due to its excellent property in dispersability of the seed crystals. The solid sorbitol forming stable crystals can be easily powdered or granulated, and the powder or granule thus obtained hardly cakes, but maintains the powdery state for long period.

EXAMPLE 4

Sorbitol powder 400 g was melted at 110° C., to which glycerol fatty acid ester (origin: cottonseed oil) 4.0 g was added with stirring, and then dispersed for 10 minutes by a homogenizer to give 10 micrometers particles. This mixture was charged into a small kneader (2 liter) with a jacket, and continuously mixed at 90° C. Into the mixture sorbitol powder of from 20 to 80 g (corresponding to 5 to 20% by weight to the melted sorbitol) were added in given amounts as seed crystals, and kneaded for 3 minutes. The kneaded sorbitol which was discharged from the kneader was pressed over on stainless steel plates kept at 50° to 80° C. at the thickness of about 3 to 5 mm so as to be solidified. The obtained sorbitol plates were maintained in thermostatic chambers adjusted to given temperatures of from 50° to 80° C. respectively, which were sampled to determine the time necessary to form stable crystals. The time is determined by Thermal Analysis System SSC 5000. The results were shown in Table 3.

TABLE 3

| quantity of seed* | temperature for treatment | | | | state of mixture before treatment |
|---|---|---|---|---|---|
| | 50° | 60° C. | 70° C. | 80° C. | |
| | period for formation of stable crystal | | | | |
| 10 wt. % | 24h | 5h | 2h | 5h | very soft rice cake like |
| 20 wt. % | 8h | 2h | 15m | 2h | very soft rice cake like |
| 30 wt. % | 4h | 1h | 15m | 1h | very soft rice cake like |

*The quantities are expressed by the percentage to the melted sorbitol.
h: hour
m: minute As apparent from Table 3 the addition of a small quantity of glycerol fatty acid ester (origin: cottonseed oil) improved the workability in the kneader and dispersability of the seed crystals. Therefore, in comparison with Example 1 (without any addition agents) the effects achieved by the seed crystals were better in the Example 4 (use of addition agents) when the same amount of the seed crystals was used, or even in case that small amount was.

What is claimed is:

1. A method of production of non-caking crystalline sorbitol which comprises stirring sorbitol seed crystals into melted sorbitol in the presence of 0.5 to 30% by weight based on the melted sorbitol of an addition agent selected from the group consisting of vegetable oils, animal oils, hardened oils, mineral oils, esters of higher fatty acids and higher fatty alcohols, glycerol fatty acid esters, sugar fatty acid esters, sorbitan fatty acid esters, propyleneglycol fatty acid esters, pentaerythritol fatty acid esters, polyglycerol fatty acid esters, polyoxyethylene sorbitan fatty acid esters, polyoxyethylene alkyl ethers, lecithin, soap of higher fatty acid, saponin, casein, polyoxyalkylene alkyl ethers, polyoxyalkylene alkylaryl ethers, polyoxyalkylene alkylamides, polyoxyethylene/polyoxypropylene random or block copolymer, sulfates of polyoxyalkylene ether type nonionic surface active agents, fatty acid esters of polyoxyalkyleneglycols, and alkylalkanolamides, and at a temperature at which the melted sorbitol does not solidify and at which the seed crystals do not melt, cooling the melted sorbitol-seed crystals mixture to about 50° C. to about 85° C. to provide solid sorbitol, aging the solid sorbitol at said temperature of about 50° C. to about 85° C., then cooling the aged solid sorbitol to room temperature, and then powdering or granulating the solid sorbitol to form the non-caking crystalline sorbitol.

2. A method of production of crystalline sorbitol according to claim 1, in which the solid is aged for five minutes or more.

3. A method of production of crystalline sorbitol according to claim 1 in which the temperature of the melted sorbitol when the seed crystals are added is controlled by the addition of the seed crystals.

4. A method of production of crystalline sorbitol according to claim 1, in which the seed crystals are added in the amount of 1 to 50% by weight based on the melted sorbitol.

5. A method of production of crystalline sorbitol according to claim 1, in which the solid is rapidly cooled to room temperature.

6. A method of production of crystalline sorbitol according to claim 1, in which the seed crystals are crystalline sorbitol or crystalline sorbitol including an addition agent selected from the group consisting of vegetable oils, animal oils, hardened oils, mineral oils, esters of higher fatty acids and higher fatty alcohols, glycerol fatty acid esters, sugar fatty acid esters, sorbitan fatty acid esters, propyleneglycol fatty acid esters, pentaerythritol fatty acid esters, polyglycerol fatty acid esters, polyoxyethylene sorbitan fatty acid esters, polyoxyethylene alkyl ethers, lecithin, soap of higher fatty acid, saponin, casein, polyoxyalkylene alkyl ethers, polyoxyalkylene alkylaryl ethers, polyoxyalkylene alkylamides, polyoxyethylene/polyoxypropylene random or block copolymer, sulfates of polyoxyalkylene ether type nonionic surface active agents, fatty acid esters of polyoxyalkyleneglycols, and alkylalkanolamides.

7. A method of production of crystalline sorbitol according to claim 1 in which the melted sorbitol is one that an addition agent selected from the group consisting of vegetable oils, animal oils, hardened oils, mineral oils, esters of higher fatty acids and higher fatty alcohols, glycerol fatty acid esters, sugar fatty acid esters, sorbitan fatty acid esters, propyleneglycol fatty acid esters, pentaerythritol fatty acid esters, polyglycerol fatty acid esters, polyoxyethylene sorbitan fatty acid esters, polyoxyethylene alkyl ethers, lecithin, soap of higher fatty acid, saponin, casein, polyoxyalkylene alkyl ethers, polyoxyalkylene alkylaryl ethers, polyoxyalkylene alkylamides, polyoxyethylene/polyoxypropylene random or block copolymer, sulfates of polyoxyalkylene ether type nonionic surface active agents, fatty acid esters of polyoxyalkyleneglycols, and alkylalkanolamides is added into.

8. A method of production of crystalline sorbitol according to claim 1, wherein the addition agent is selected from the group consisting of vegetable oils and animal oils.

9. A method of production of crystalline sorbitol according to claim 6, in which the seed crystals are crystalline sorbitol or crystalline sorbitol including an addition agent selected from the group consisting of vegetable oils and animal oils.

10. A method of production of crystalline sorbitol according to claim 1, in which the melted sorbitol is one that an addition agent selected from the group consisting of vegetable oils and animal oils is added into.

* * * * *